United States Patent
Forsell

(10) Patent No.: US 10,821,289 B2
(45) Date of Patent: Nov. 3, 2020

(54) IMPLANTABLE DEVICE FOR EXTERNAL URINARY CONTROL

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 15/917,978

(22) Filed: Mar. 12, 2018

(65) Prior Publication Data
US 2018/0263840 A1 Sep. 20, 2018

Related U.S. Application Data

(63) Continuation of application No. 15/168,117, filed on May 30, 2016, now Pat. No. 9,913,774, which is a continuation of application No. 12/682,517, filed as application No. PCT/SE2008/000560 on Oct. 11, 2008, now Pat. No. 9,351,664.

(60) Provisional application No. 60/960,715, filed on Oct. 11, 2007, provisional application No. 60/960,716, filed on Oct. 11, 2007.

(51) Int. Cl.
| | | |
|---|---|---|
| A61H 9/00 | (2006.01) | |
| A61N 1/378 | (2006.01) | |
| A61N 1/372 | (2006.01) | |
| A61B 5/02 | (2006.01) | |
| A61B 5/07 | (2006.01) | |
| A61B 5/00 | (2006.01) | |
| A61B 17/12 | (2006.01) | |
| A61B 17/135 | (2006.01) | |
| A61N 1/05 | (2006.01) | |
| A61B 17/00 | (2006.01) | |
| A61F 2/30 | (2006.01) | |
| A61B 90/00 | (2016.01) | |

(52) U.S. Cl.
CPC ...... *A61N 1/37252* (2013.01); *A61B 5/02007* (2013.01); *A61B 5/076* (2013.01); *A61B 5/4393* (2013.01); *A61B 5/6862* (2013.01); *A61B 5/6876* (2013.01); *A61B 5/6885* (2013.01); *A61B 17/12009* (2013.01); *A61B 17/1355* (2013.01); *A61H 9/00* (2013.01); *A61N 1/0556* (2013.01); *A61N 1/3787* (2013.01); *A61B 2017/00221* (2013.01); *A61B 2017/00411* (2013.01); *A61B 2017/00703* (2013.01); *A61B 2017/00734* (2013.01); *A61B 2090/065* (2016.02); *A61B 2562/0247* (2013.01); *A61B 2562/0261* (2013.01); *A61F 2002/3067* (2013.01); *A61F 2002/30668* (2013.01); *A61F 2250/0001* (2013.01); *A61F 2250/0002* (2013.01); *A61H 2201/1207* (2013.01); *A61H 2201/1238* (2013.01)

(58) Field of Classification Search
None
See application file for complete search history.

(56) References Cited

U.S. PATENT DOCUMENTS

2004/0242956 A1* 12/2004 Scorvo .................. A61F 2/0022
600/30

* cited by examiner

*Primary Examiner* — Christine H Matthews
*Assistant Examiner* — Joshua Daryl D Lannu

(57) ABSTRACT

The present invention relates to an implantable apparatus for obtaining urinary control and emptying of the urinary bladder. The apparatus operates with a powered member operating from the outside of the urinary bladder assisted by a support structure to discharge urine from the urinary bladder. A control device controls the operation of the powered member. The control device further comprises a source of energy for operating the powered member and other energy consuming parts of the apparatus and a control assembly.

20 Claims, 15 Drawing Sheets

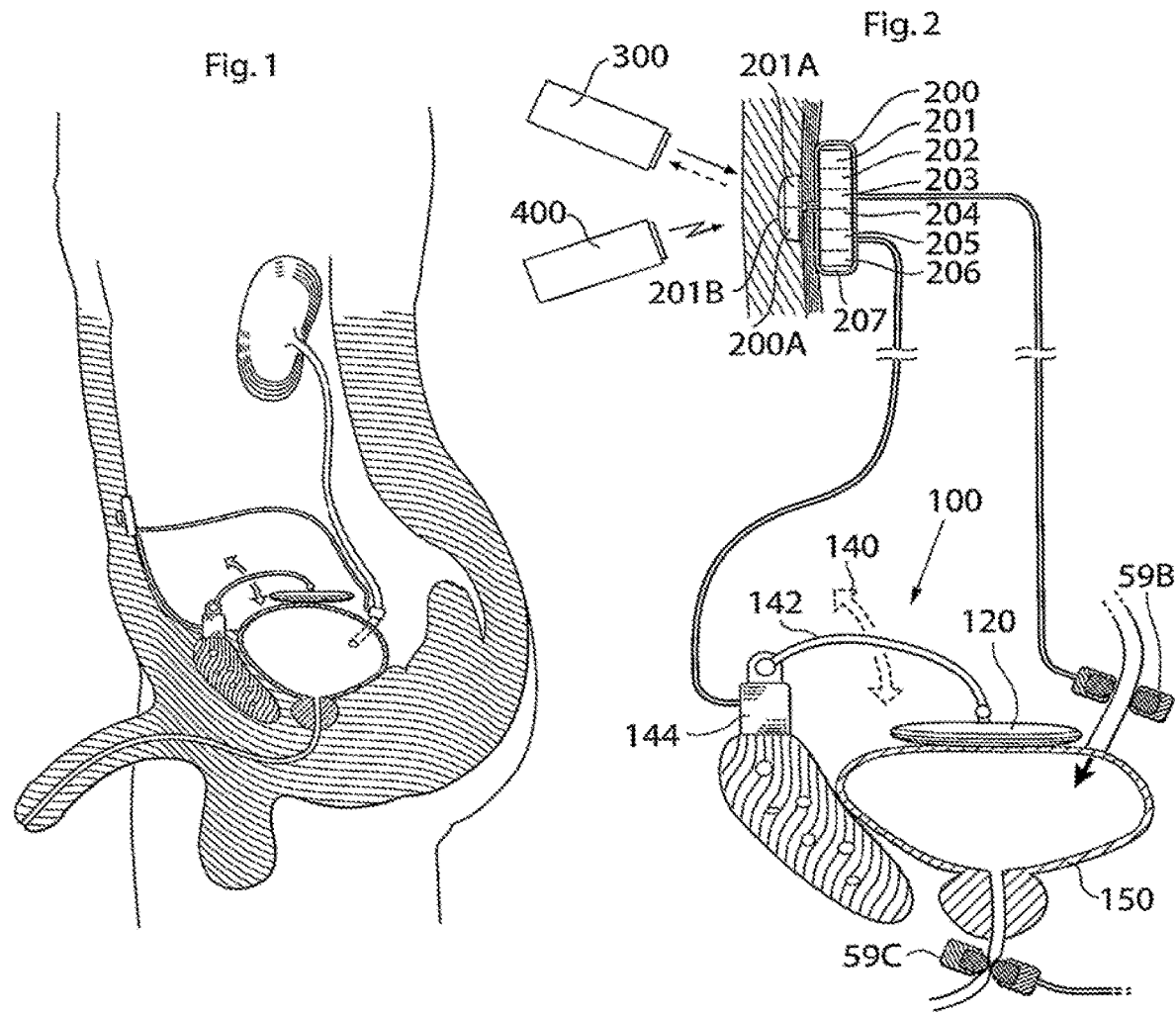
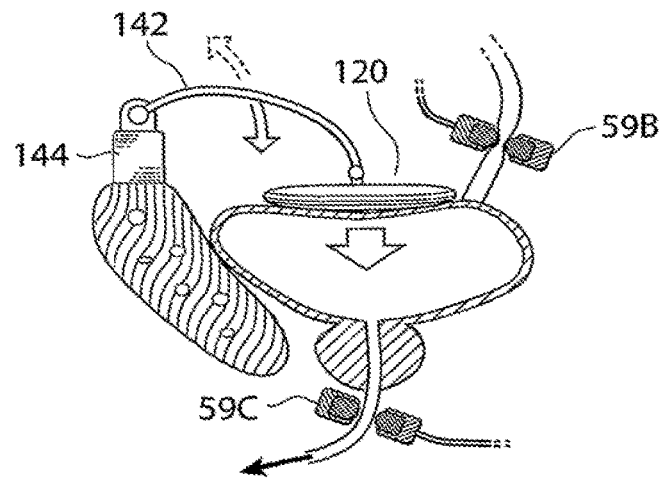

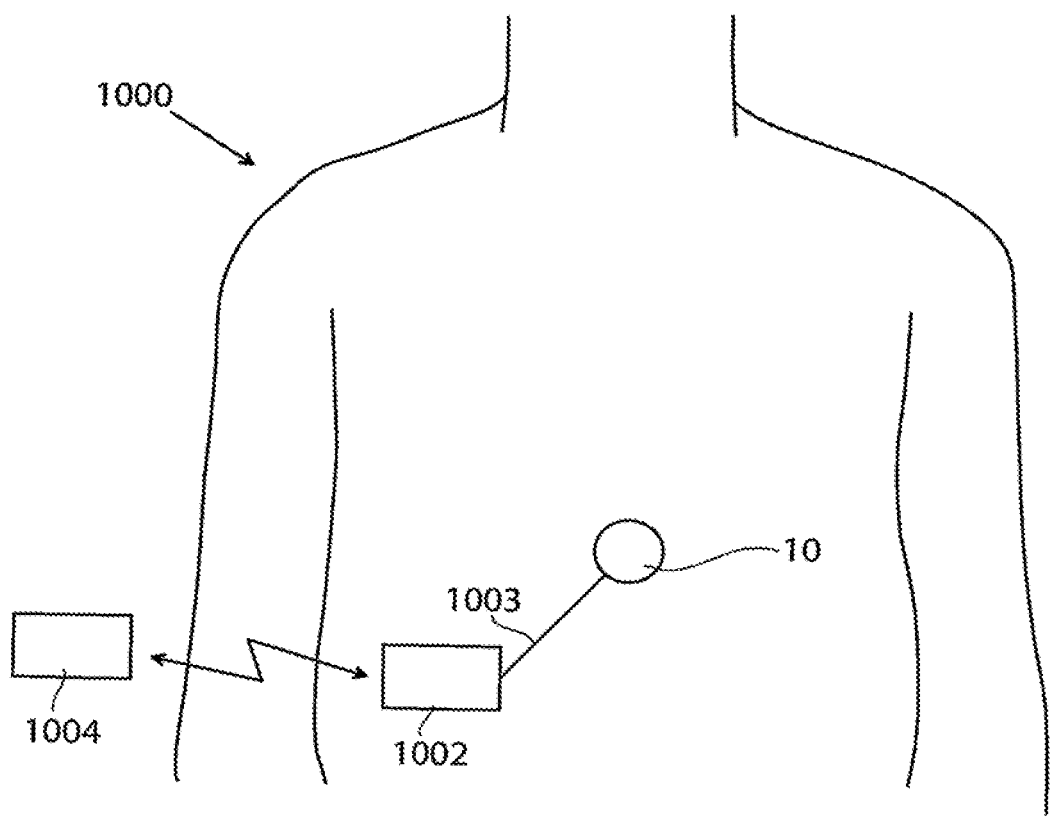

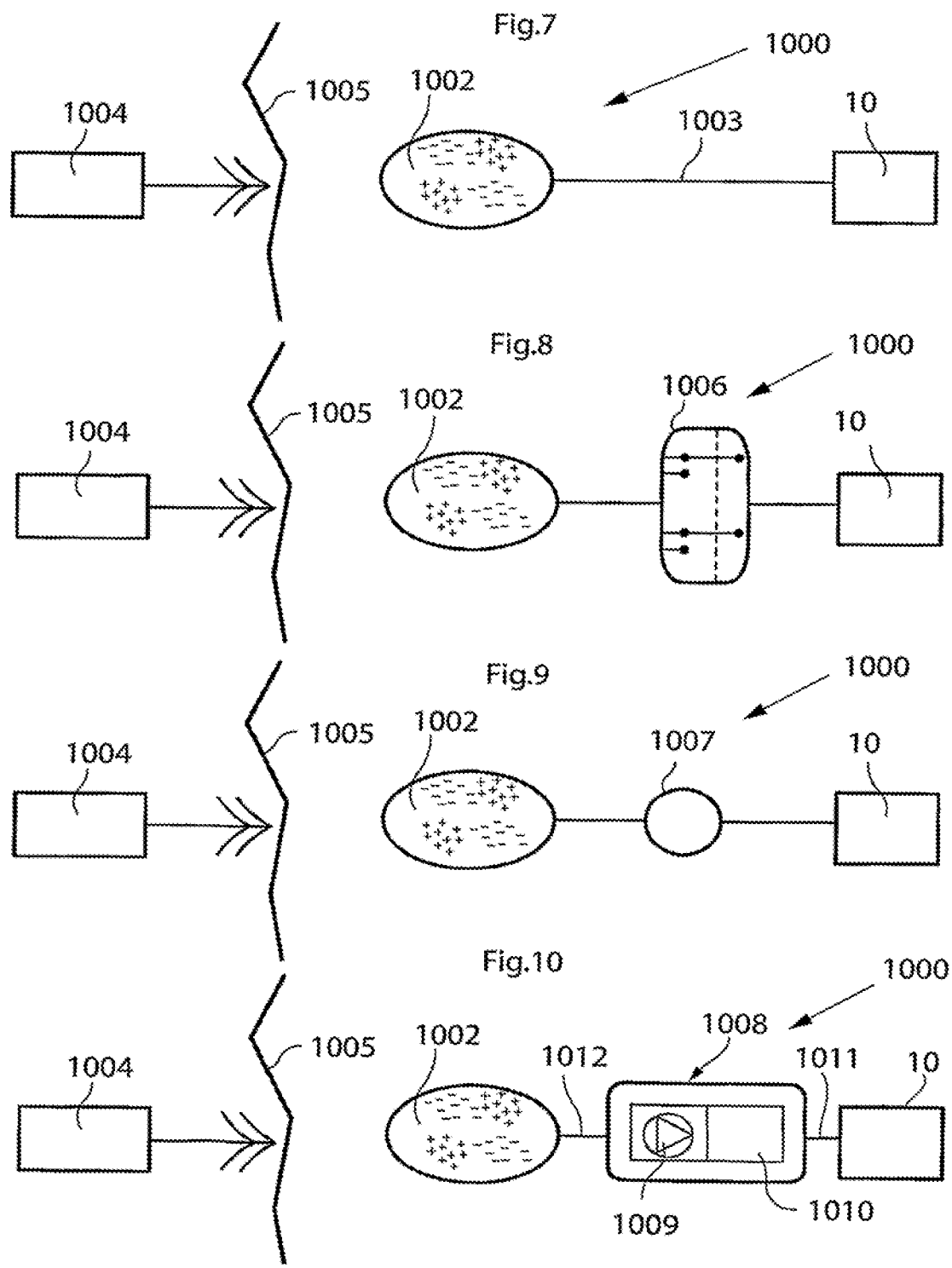

IMPLANTABLE DEVICE FOR EXTERNAL URINARY CONTROL

This application is a continuation of U.S. patent application Ser. No. 15/168,117, filed May 30, 2016, which is a Continuation of U.S. patent application Ser. No. 12/682,517, filed on Apr. 9, 2010 and issued on May 31, 2016 as U.S. Pat. No. 9,351,664, which is the National Stage Entry of PCT/SE2008/00560, filed on Oct. 11, 2008, now expired, which claims the benefit of Provisional Patent Applications 60/960,715 and 60/960,716, both filed Oct. 11, 2007, all of which are hereby incorporated by reference.

FIELD OF INVENTION

The present invention relates to an implantable apparatus for obtaining urinary control and emptying of the urinary bladder, thereby preventing from or treating involuntary urinary retention. More particularly, the invention relates to an implantable apparatus for discharging urine from the urinary bladder with a powered member operating from the outside of the urinary bladder assisted by a support structure.

BACKGROUND OF INVENTION

Urinary dysfunction commonly caused by spinal cord injuries involves involuntary urinary retention, a condition which associated with urinary infections, renal damages or damages to the urinary tract. A common treatment of urinary retention is continuous or intermittent catheterization. Besides the inconvenience for the patient, catheters always represent a risk of acquiring infections. Alternatively suggested therapies include electric stimulation of the urinary bladder for providing muscle contraction and bladder emptying (see e.g. U.S. Pat. No. 6,393,323). Electric stimulation of the bladder needs consideration to that the urinary sphincter is stimulated to contraction by electricity and pulsed stimulation will become necessary which, however, may lead to uncontrolled squirts of urine through the urethra. It is obvious that there is a need for devices assisting with urinary bladder voiding which are efficient, reliable and that provide a high level of patient compliance.

DESCRIPTION OF INVENTION

In general terms, the present invention relates to an apparatus for treating urinary retention of a mammal patient, comprising an implantable powered member adapted exert a force from the outside on a selected part of the urinary bladder in order to discharge urine from the urinary bladder. The apparatus further comprises a control device for controlling the operation of the powered member. The force of the powered member is exerted at least partly against a support structure which is adapted to support against at least one of, a bone, such as the pelvic bone, pubic bone or sacrum or spinal cord, other human tissue such as peritoneum, the abdominal or pelvic wall, or the urine bladder itself.

The control device preferably comprises a source of energy for operating the powered member and other energy consuming parts of the apparatus. Arrangements for energizing and controlling the apparatus in the context of a system comprising the apparatus will be disclosed below. The control device preferably is adapted to be implanted at least partly subcutaneously or in the abdomen or in the pelvic region. The control device comprises a control assembly adapted to be implanted both subcutaneously and/or in the abdominal cavity, said control assembly comprising at least two parts adapted to be connected, when implanted.

In order to actuate the urinary bladder from the outside, the powered member comprises a contacting part adapted to contact a surface part of the urinary bladder. The powered member comprises at least one operable pressurizer connected to the contacting part in an arrangement, wherein operating the pressurizer provides compression or release of the urinary bladder. For this purpose, the powered member can be hydraulically or mechanically operated to provide compression or release of the urinary bladder.

In one embodiment, the pressurizer comprises at least one movable an extending from an operation device to the contacting part of the powered member. The operation device is adapted to displace the movable arm towards the urinary bladder in order to discharge urine from the urinary bladder. The operation device is fixated to human tissue, preferably in this embodiment, to the pubic bone. Further in this embodiment, the operation device comprises a motor, preferably an electric motor adapted to displace the movable arm. The contacting part is adapted be fixated to the upper part of urinary bladder and the contacting part preferably is designed to extend radially from a point essentially in line with the urinary bladder apex.

In another embodiment, the pressurizer comprises a reservoir for hydraulic fluid, and the contacting part comprises an expandable cavity hydraulically connected to the reservoir. The pressurizer comprises a pump for transporting the hydraulic fluid from the reservoir to expand the expandable cavity thereby compressing the urinary bladder. Further, the pressurizer is adapted to have the hydraulic fluid transported from the expandable cavity to the reservoir by the urinary pressure in the urinary bladder, when the pump is not active. In order to accomplish transportation back from the cavity to the reservoir, an arrangement can be provided wherein a second connection between the expandable cavity and the reservoir adapted to admit transportation hydraulic fluid from the expandable cavity to the reservoir by the urinary pressure in the urinary bladder, when the pump is not active. Preferably, the flow capacity of the second connection is smaller than the pump flow, allowing said second connection to stand open. Alternatively to this arrangement, the pump can transport hydraulic fluid from the expandable cavity to the reservoir in order to release the urinary bladder.

In still another embodiment, the operable pressurizer comprises an operation device attached to a support device adapted to be fixated to the urinary bladder wall. The operable pressurizer comprises an actuator operably connected to the operation device comprising a motor to perform an actuating movement to actuate the contacting part to compress the urinary bladder. Preferably, the operation device comprises a pivot for accomplishing a pivotal movement of actuator. The support device is generally ring-shaped or having an intermittent ring-shape and extends along the periphery of the urinary bladder.

The apparatus as embodied in previous sections further can comprise a device for electrically stimulating the muscles of the urinary bladder to contract. Such a stimulating device can comprise a plurality of electrode strips attached to the muscles of the urinary bladder.

The apparatus as embodied in previous sections can also comprise an implantable pair of restriction devices, wherein the control device controls the restriction devices adapted to close the ureters when discharging urine from the urinary bladder.

The apparatus as embodied in previous sections can also comprise an artificial urinary sphincter, wherein a restriction device, controlled by the control device performs as a urinary sphincter.

The apparatus as embodied in previous sections can also comprise a sensor for measuring any parameter related to the urinary pressure or volume of the urinary bladder. The sensor is capable of sending a signal to the control device, which thereby activates and deactivates the powered member.

The present invention also relates to a method of implanting the disclosed apparatus that comprises the steps of inserting a needle-like tube into the abdomen of the patient; filling the abdomen with gas through said tube, thereby expanding the abdominal cavity; placing at least two laparoscopic trocars in the patient's body and inserting a camera through one of said trocars into the abdomen; inserting at least one dissecting tool through a trocar and dissecting an area of at least one portion of the urinary bladder of patient; fixating a first part of the powered member to the urinary bladder; fixating another, different part of the powered member to human tissue and implanting the control device connected to the powered member. In the method the first part of the powered member is a contacting part contacting a surface part of the urinary bladder and the different part of the powered member is fixed to the pubic bone, or the abdominal wall, or the urinary bladder wall. When fixating the different part to the urinary wall it is preferred to tunnelling by suturing the urinary bladder wall to itself in order to immobilize the different part, while the urinary wall includes or not includes the peritoneum. Preferably, the different park comprises generally ring shaped support device which preferably extends along periphery of the urinary bladder.

The present invention further relates to an alternative method for implanting the apparatus, comprises the steps of cutting the skin; dissecting an area of at least one portion of the urinary bladder of patient; fixating a first part of the powered member to the urinary bladder; fixating another, different part of the powered member to human tissue and implanting the control device connected to the powered member. In the method the first part of the powered member is a contacting part contacting a surface part of the urinary bladder and the different part of the powered member is fixed to the pubic bone, or the abdominal wall, or the urinary bladder wall; placing a control device outside the urinary bladder. The method further may include at least one of the following steps of placing a power source within the body, for powering the control device;

placing a hydraulic reservoir and; placing a pump within the body, for pumping fluid between the reservoir and the expandable member to discharge urine from the urine bladder.

The present invention further relates to system comprising a previous embodies apparatus according to any of claims.

In a preferred embodiment, the system comprises at least one switch implantable in the patient for manually and non-invasively controlling the apparatus In another preferred embodiment, the system comprises a wireless remote control for non-invasively controlling the apparatus.

In a preferred embodiment, the system comprises a hydraulic operation device for operating the apparatus.

In one embodiment, the system comprises comprising a motor or a pump for operating the apparatus.

Further details of the systems applicable with the apparatus as generally described herein are outlined below in the detailed description.

DETAILED DESCRIPTION OF INVENTION

The present invention will now be described in more detail by way of non-limiting examples and with reference to the accompanying drawings, in which:

FIG. 1 shows a schematic crossectional view of an embodiment of the apparatus of invention when implanted in a patient.

FIGS. 2 and 3 schematically show an embodiment of the apparatus with a first variant of the powered member.

FIGS. 4 and 5A to C schematically show respectively different embodiments of the pressurizer of the powered member.

FIG. 6 illustrates a system including an apparatus for treating urinary incontinence according to invention as generally described or illustrated in FIGS. 1 to 5 here in a general form.

FIGS. 7-21 schematically show various embodiments of the system for wirelessly powering the apparatus shown in FIG. 1.

FIG. 22 is a schematic block diagram illustrating an arrangement for supplying an accurate amount of energy used for the operation of the apparatus shown in FIG. 1.

FIG. 23 schematically shows an embodiment of the system, in which the apparatus is operated with wire bound energy.

DETAILED DESCRIPTION OF PREFERRED EMBODIMENTS

Figure 4A:
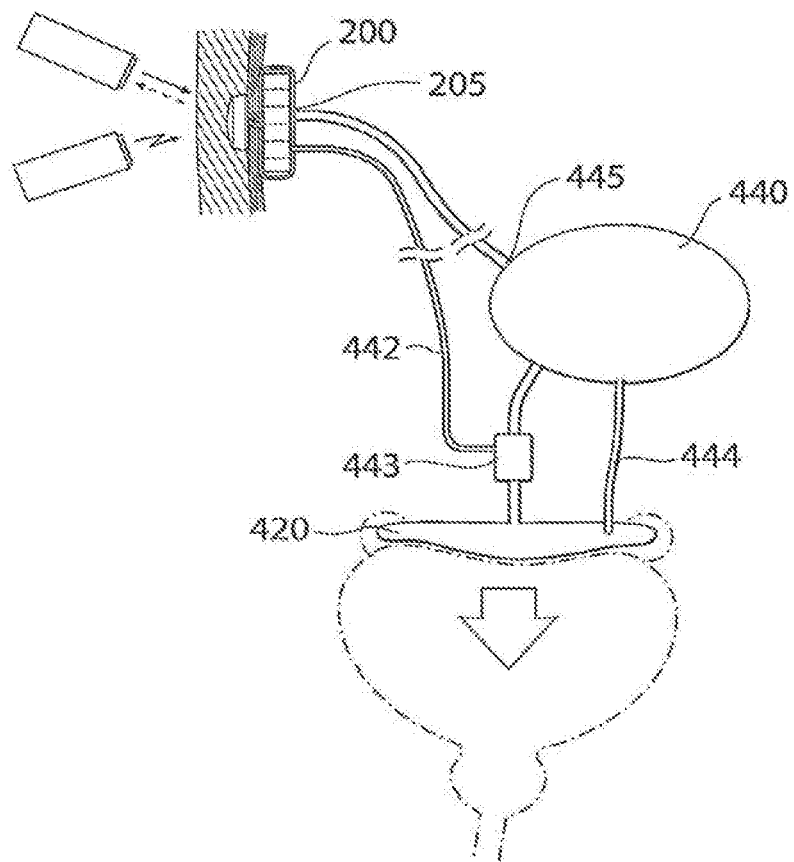

FIG. 1 is a general crossectional view of the apparatus when implanted in a human patient. Referring to FIG. 2 an embodiment of the apparatus is shown as implanted when operating on a urinary bladder 300. The apparatus includes a powered member 100 and a control device 200. The controls device 200 controls the operation of the powered member and is capable of receiving a signal from a sensor 150 related to the volume in the urine bladder such as a pressure sensor or any sensor related to the wall of the urine bladder (not shown and to communicate out from the body an alarm signal. The sensor is connected to sensor control unit 205 of the control device 200. Several different types of input sensors may be used determining for example stretching or bending or pressure in the urine bladder wall or for example sensing volume or pressure inside the urine bladder. Most likely these sensors is only indirect causing the bladder to be emptied by presenting an alarm for the patient informing that it is time to empty the bladder. Such an alarm may be generated audible or visually. A remote control 300 controlled from outside body of the patient in order to operate the powered member, such as a wireless remote control communicating with an internal control unit 203 or at least one implanted switch 204. The control device 200 also includes an energy source 201 for supplying energy consuming parts of the powered member with energy. The energy source can be wirelessly supplied from the outside from an energizer unit 400. For this purpose the control device is provided with an energy transforming device 202. The control device comprises an external part 200A which is provided a manually operated switch 201A and with an injection port 201B for hydraulic fluids communicating with an internal reservoir 206. The control device further includes a motor/pump function. It is contemplated that the features related to hydraulic fluid is relevant for a hydraulic embodiment of FIG. 4 and the powered member 100 includes a pressurizer 140 and a urinary bladder contact part 120 which may be fixated to the urinary bladder. The pressurizer includes an operation device 144 fixated to human tissue in this case the pubic bone and is operative connected to movable arm 142 connected to the contacting part. In operation to exert a pressure on the urinary bladder and thereby discharging urine through the urethra, the operation device 144 is activated by control device to move the arm towards the urinary bladder which thereby is contracted. Further FIG. 2 shows a restriction device 59B for temporarily restriction of a ureter (this embodiment closes both ureters with restriction devices). The apparatus may eventually be provided with such restriction devices for the ureters which are controlled by the control device 200 to close the ureters when operating the powered member to discharge wine in order to prevent from a urinary flow from the bladder to the kidneys. In operation the control device 200 is activated and supplies the powered member with energy. The pressurizer will then actuate the urinary bladder to compress so the urinary pressure in the bladder is raise so urine is discharges through the urethra. When the urinary discharge is finalized the pressurizer alleviates the urinary and returns to its initial position, while the restriction devices for the ureters are released and the urinary bladder can receive urine from the kidneys. FIG. 3 shows the same apparatus as FIG. 2 when discharging urine through urethra. For this purpose the urinary sphincter 59C is deactivated an open and the restriction device 59B. The apparatus needs to exert a considerable pressure (about 60-80 cm water pressure) to force urine out from the bladder and urine may thereby backflow through ureters 32A, 32B with potential risks for damaging the kidneys. To prevent from any such complications, the control device is provided with restriction devices 59A, 59B arranged to temporarily contract the ureters and close them during the operation of discharging urine. The urine pressure in the ureter is normally around 50 cm water, however short term pressure increase is most likely not damaging the kidneys and therefore the restriction devices 59A and 59B may be omitted.

Figure 4B:
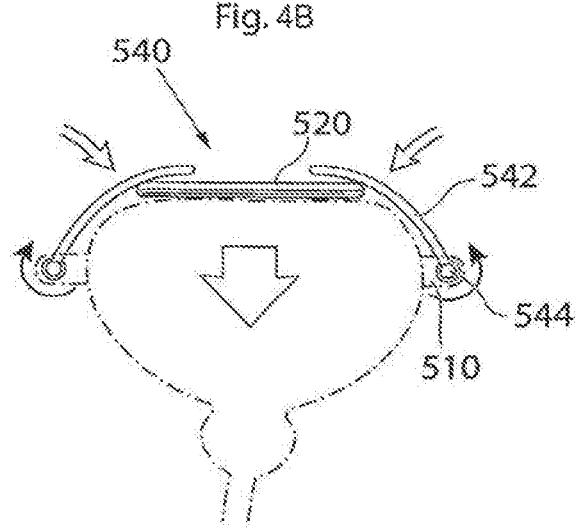
Figure 5:
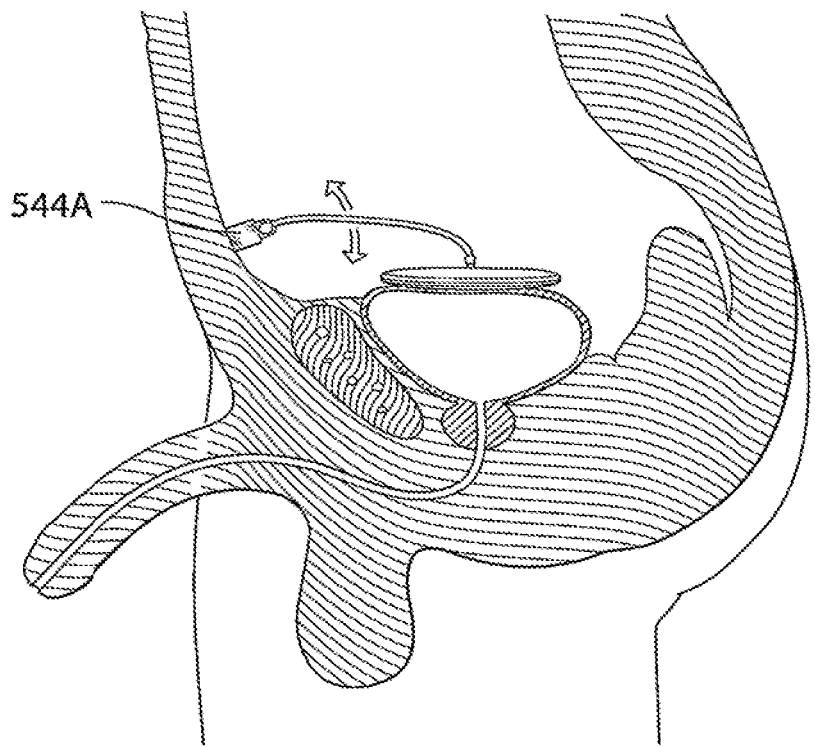
Figure 5:
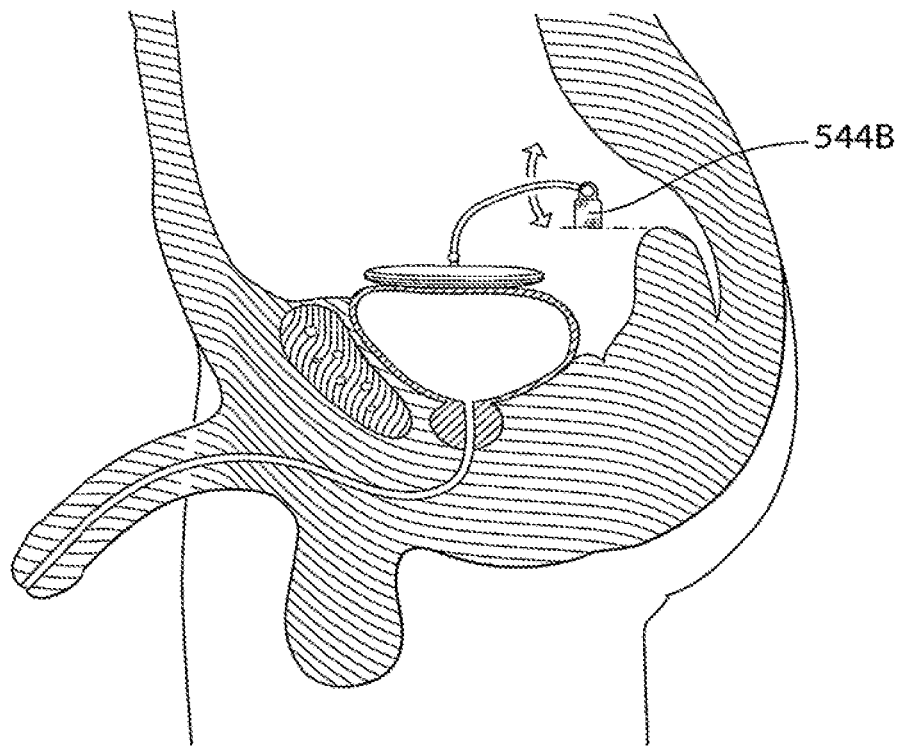
Figure 5:
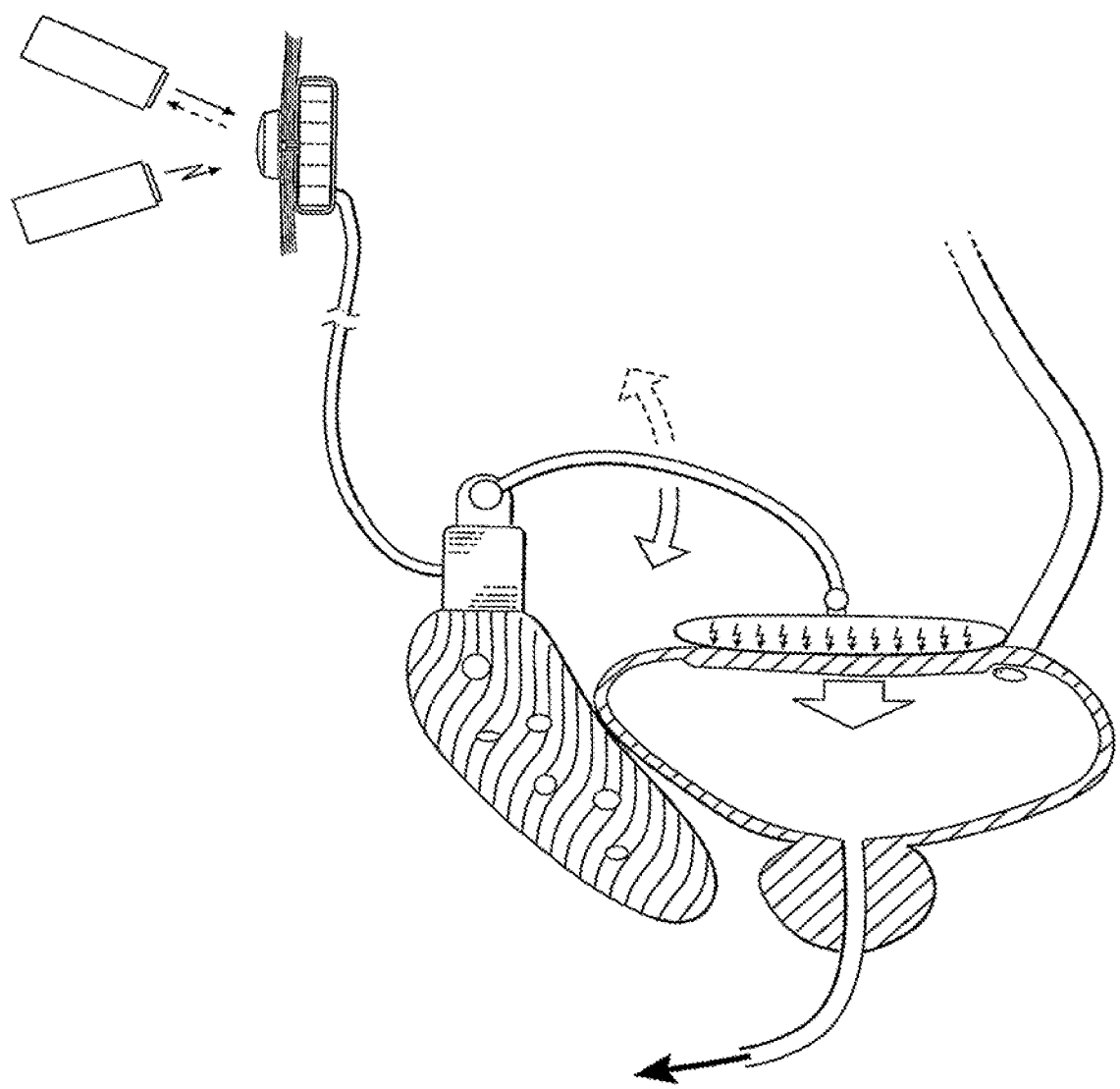

FIG. 4 shows schematically a variant of the pressurizer which now includes reservoir 440 that is hydraulically connected to a cavity 420 of the contacting part. A control device 200 controls the operation of the pressurizer in a similar way as explained with FIG. 2. When operating the apparatus to discharge urine the control device activates transportation of fluid from the reservoir 440 to the cavity 420 of the contacting part which thereby expands in volume so the urinary bladder compresses and urine is discharge through the urethra as a consequence of a raised urinary pressure in the bladder. In order to release the bladder, fluid is transported back to the reservoir from the cavity. The back transportation can either be performed by a powered operation (i.e. a pump operatively connected to the reservoir) or as result of the raising urinary pressure in the bladder. A second connection 444 between the cavity and the reservoir is used for the later transport. If the pump pumping capacity is larger than the flow capacity of said second connection the second connection may be opened all the time. FIG. 4 further sows a sensor 445 communicating with control device sensor control unit. FIG. 5 shows schematically another variant of the pressurizer 540 including an operation device 544 attached to a support device 510 fixated to the urinary bladder wall. The pressurizer may be both hydraulically or mechanically operated. In this case a mechanical construction has an actuator 542 operably connected to the operation device to perform an actuating movement to actuate the contacting part 520 to compress the urinary bladder. In operation to discharge urine, the operation device performs a pivotal movement of the actuator so it contacts the contact part 520 to compress the urinary bladder in order to discharge urine through the urethra. When releasing the bladder the operation device removes the actuator 542 from the contacting part 520 to its initial position and the urinary bladder is ready to receive urine through the ureters.

FIG. 5a shows an embodiment of the apparatus of FIG. 2 with the operation device 544A placed on the abdominal wall as an alternative support function. FIG. 5b shows another alternative of the apparatus of FIG. 2 with the operation device supported another bone structure. FIG. 5c shows an alternative of the apparatus of FIG. 2 without restriction devices for the ureters and without a urinary sphincter function.

Some patients having urinary retention also have urinary incontinence. In such a case a separate urinary sphincter 59C is included in the system, a restriction device closing the urethra until the patient wants to urinate. In such a case lower pressure is needed to empty the bladder because the no force would be needed to open the sphincter by intra bladder pressure. In this case the ureter restriction devices may be omitted.

The reservoir may be placed anywhere inside the body, however preferable in the abdominal cavity, maybe placed onto the urine bladder or in the pelvic region. The amount of liquid in the reservoir may be calibrated with fluid by using an injection port placed inside the body within reach from a special injection port needle. The reservoir may also be omitted and only the injection port may be used to fill and empty the expandable member.

FIG. 6 illustrates a system for treating urinary retention with an apparatus 10 of the present invention schematically shown placed in the abdomen of a patient. The apparatus 10 can be any of those discussed in the context of FIGS. 1-5 or as generally described in previous section of the description. An implanted energy-transforming device 1002 is adapted to supply energy consuming components of the apparatus with energy via a power supply line 1003. An external energy-transmission device 1004 for non-invasively energizing the apparatus 10 transmits energy by at least one wireless energy signal. The implanted energy-transforming device 1002 transforms energy from the wireless energy signal into electric energy which is supplied via the power supply line 1003.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted apparatus 10 is operable in response to the energy of the second form. The energy-transforming device 1002 may directly power the apparatus with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the apparatus, as the wireless energy is being transmitted by the energy-transmission device 1004. Where the system comprises an operation device for operating the apparatus, as will be described below, the wireless energy transmitted by the energy-transmission device 1004 may be used to directly power the operation device to create kinetic energy for the operation of the apparatus.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 1004 also includes a wireless remote control having an external signal transmitter for transmitting a wireless control signal for non-invasively controlling the apparatus. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 7 illustrates the system of FIG. 6 in the form of a more generalized block diagram towing the apparatus 10, the energy-transforming device 1002 powering the apparatus 10 via power supply line 1003, and the external energy-transmission device 1004, The patient's skin 1005, generally shown by a vertical line, separates the interior of the patient to the right of the line from the exterior to the left of the line.

FIG. 8 shows an embodiment of the invention identical to that of FIG. 7, except that a reversing device in the form of an electric switch 1006 operable for example by polarized energy also is implanted in the patient for reversing the apparatus 10. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the apparatus 10.

FIG. 9 shows an embodiment of the invention identical to that of FIG. 7, except that an operation device 1007 implanted in the patient for operating the apparatus 10 is provided between the implanted energy-transforming device 1002 and the apparatus 10. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 10 shows an embodiment of the invention identical to that of FIG. 7, except that it also comprises an operation device is in the form of an assembly 1008 including a motor/pump unit 1009 and a fluid reservoir 1010 is implanted in the patient, in this case the apparatus 10 is hydraulically operated, i.e. hydraulic fluid is pumped by the motor/pump unit 1009 from the fluid reservoir 1010 through a conduit 1011 to the apparatus 10 to operate the apparatus, and hydraulic fluid is pumped by the motor/pump unit 1009 back from the apparatus 10 to the fluid reservoir 1010 to return the apparatus to a starting position. The implanted energy-transforming device 1002 transforms wireless energy into a current, for example a polarized current, for powering the motor/pump unit 1009 via an electric power supply line 1012.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 11:
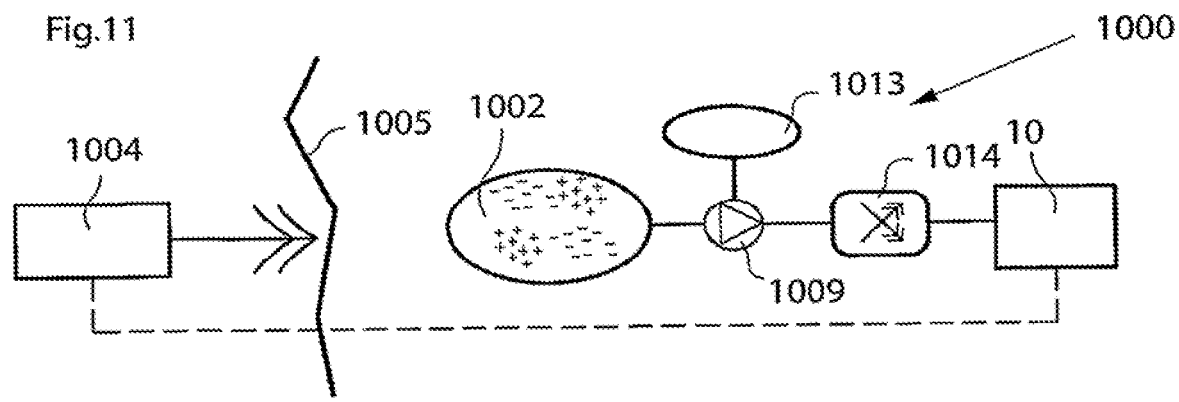

FIG. 11 shows an embodiment of the invention comprising the external energy-transmission device 1004 with its wireless remote control, the apparatus 10, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the apparatus 10. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the apparatus 10 to operate the apparatus, and another opposite direction in which the fluid is pumped by the motor/pump unit 1009 back from the apparatus 10 to the hydraulic fluid reservoir 1013 to return the apparatus to a starting position.

Figure 12:
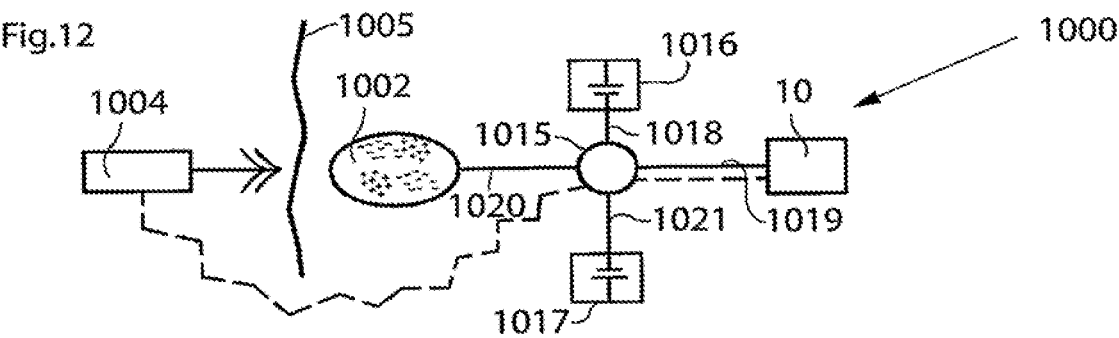

FIG. 12 shows an embodiment of the invention comprising the external energy-transmission device 1004 with its wireless remote control, the apparatus 10, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the apparatus 10. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 1017 in the embodiment of FIG. 12 may be omitted. In accordance with another alternative, the accumulator 1016 in this embodiment may be omitted.

Figure 13:
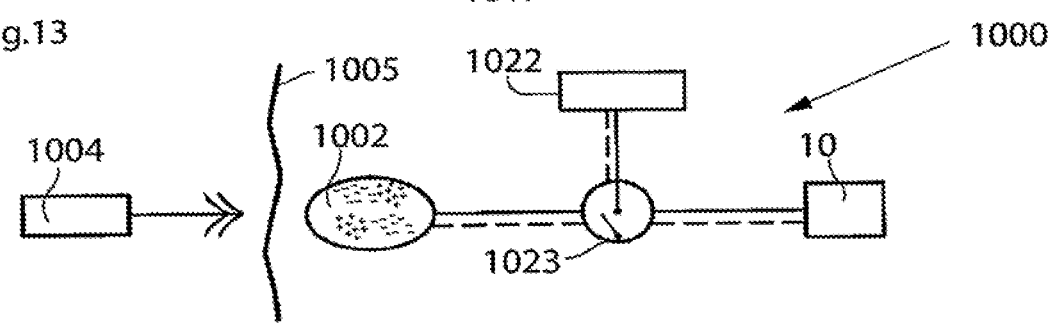

FIG. 13 shows an embodiment of the invention identical to that of FIG. 7, except that a battery 1022 for supplying energy for the operation of the apparatus 10 and an electric switch 1023 for switching the operation of the apparatus 10 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the apparatus 10.

Figure 14:
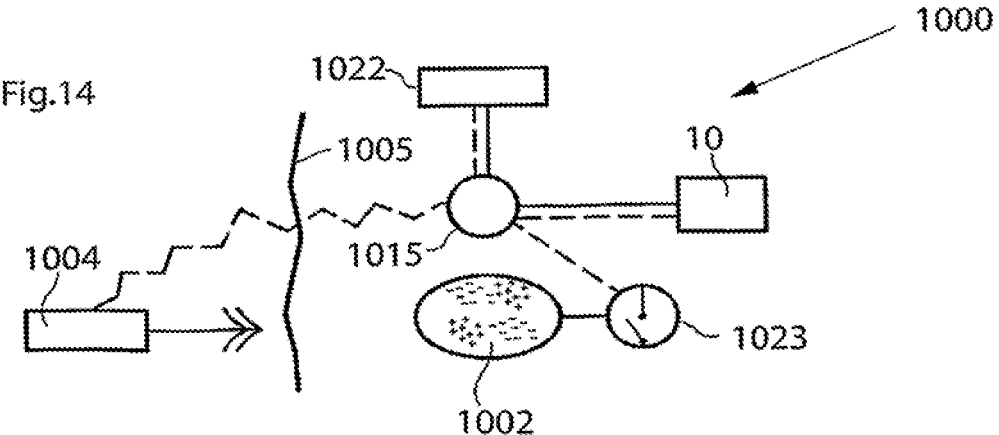

FIG. 14 shows an embodiment of the invention identical to that of FIG. 13, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the apparatus 10.

Figure 15:
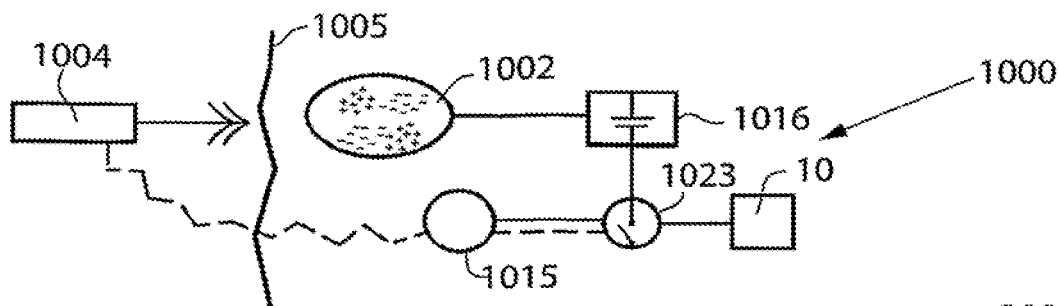

FIG. 15 shows an embodiment of the invention identical to that of FIG. 14, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the apparatus 10. The accumulator may be combined with or replaced by a capacitor.

Figure 16:
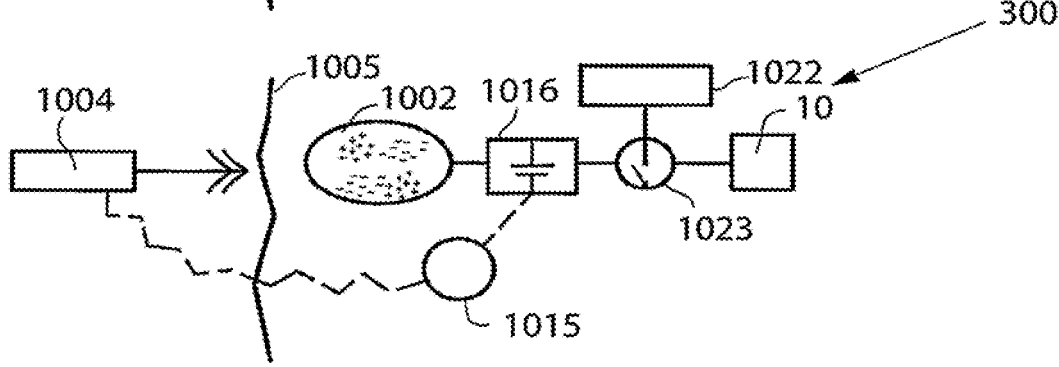

FIG. 16 shows an embodiment of the invention identical to that of FIG. 15, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the apparatus 10.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the apparatus 10.

It should be understood that the switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 17:
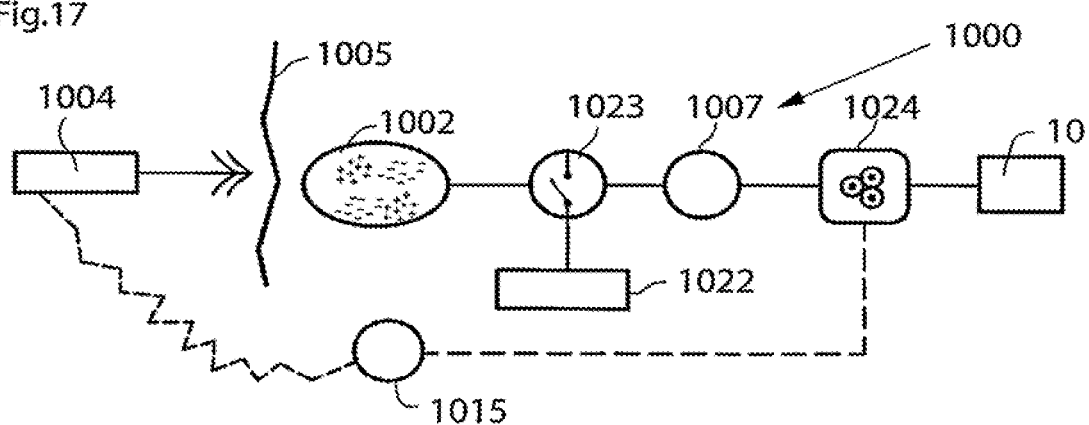

FIG. 17 shows an embodiment of the invention identical to that of FIG. 13, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the apparatus 10 (mechanically operated). Even simpler is to switch the direction of the motor electronically. The gear box interpreted in its broadest embodiment may stand for a servo arrangement saving force for the operation device in favour of longer stroke to act.

Figure 18:
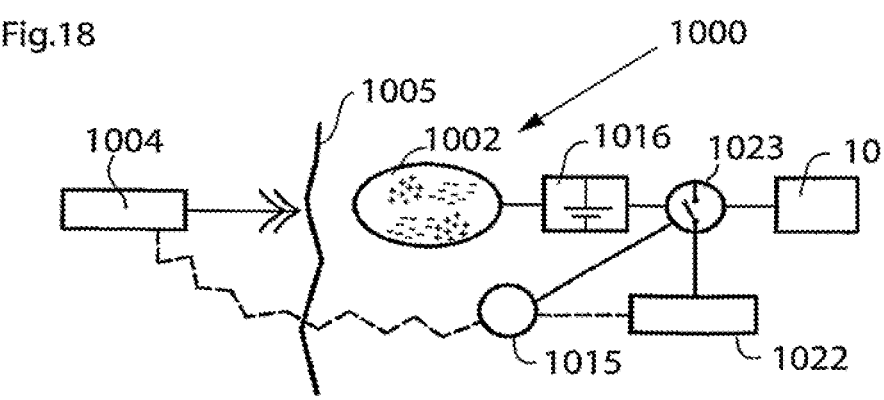
Figure 24:
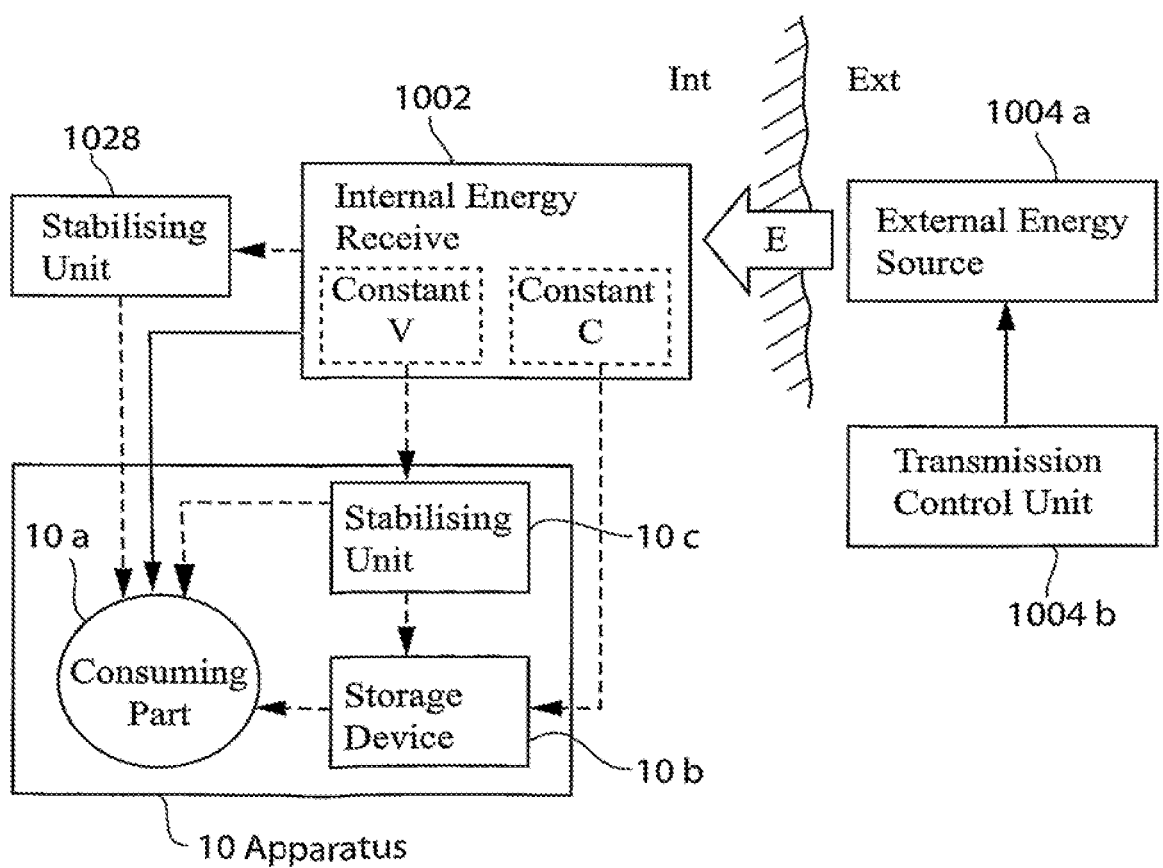
FIG. 24 is a more detailed block diagram of an arrangement for controlling the transmission of wireless energy used for the operation of the apparatus shown in FIG. 1.

FIG. 18 shows an embodiment of the invention identical to that of FIG. 24 except that the implanted components are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the apparatus 10.

Figure 19:
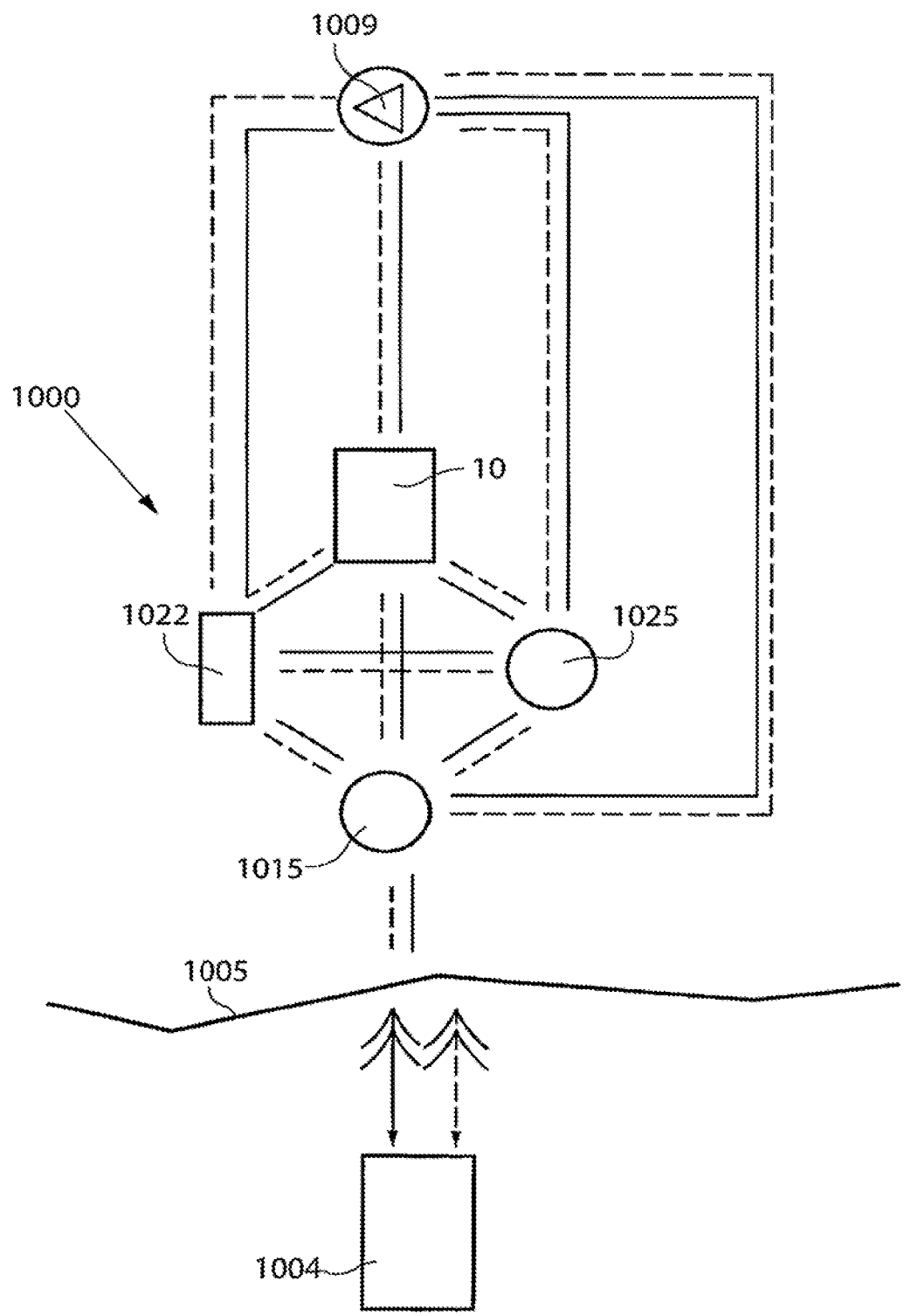

FIG. 19 schematically shows conceivable combinations of implanted components of the apparatus for achieving various communication options. Basically, there are the apparatus 10, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the apparatus.

A feedback device, preferably comprising a sensor or measuring device 1025, may be implanted in the patient for sensing a physical parameter of the patient. The physical parameter may be at least ore selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, strete, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the apparatus 10 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the apparatus 10 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feed back information related to said charging process is sent and the energy supply is changed accordingly.

Figure 20:
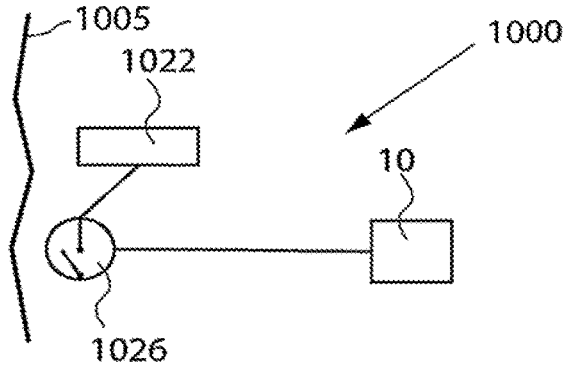

FIG. 20 shows an alternative embodiment wherein the apparatus 10 is regulated from outside the patient's body. The system 1000 comprises a battery 1022 connected to the apparatus 10 via a subcutaneous electric switch 1026. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

Figure 21:
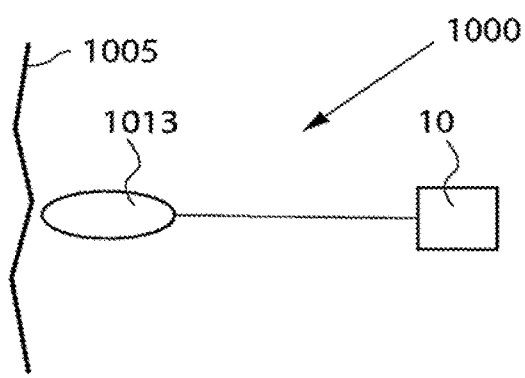

FIG. 21 shows an alternative embodiment, wherein the system 1000 comprises a hydraulic fluid reservoir 1013 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

Figure 22:
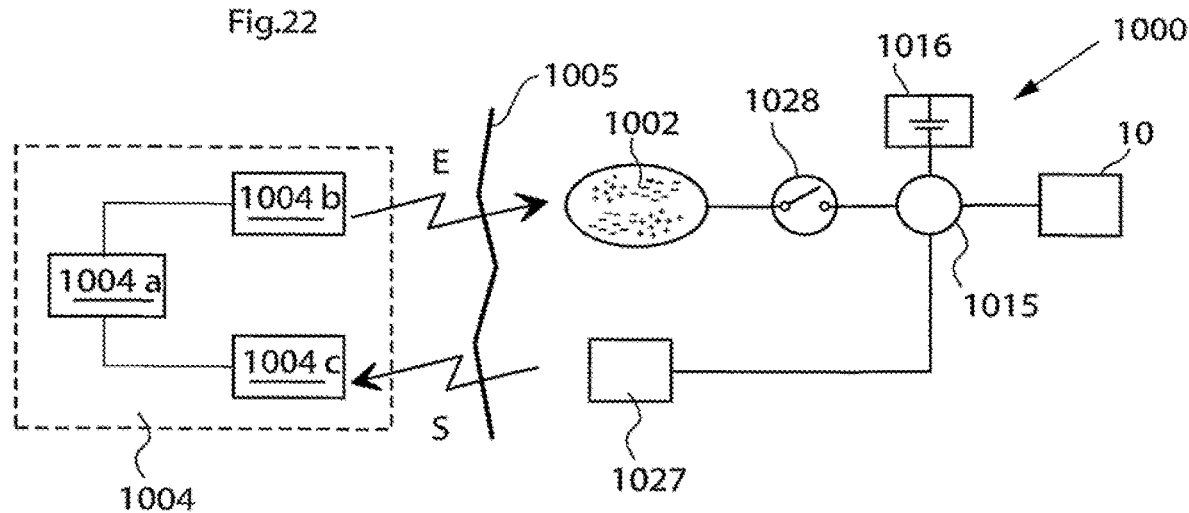

FIG. 22 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 1002 connected to implanted energy consuming components of the apparatus 10. Such an energy receiver 1002 may include an energy source and/or an energy-transforming device. Briefly described, wireless energy is transmitted from an external energy source 1004*a* located outside the patient and is received by the internal energy receiver 1002 located inside the patient. The internal energy receiver is adapted to directly or indirectly supply received energy to die energy consuming components of the apparatus 10 via a switch 1026. An energy balance is determined between the energy received by the internal energy receiver 1002 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 22 the patient's skin is indicated by a vertical line 1005. Here, the energy receiver comprises an energy transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy F transmitted from the external energy-source 1004*a* provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004*a* and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004*b* that controls the external energy source 1004*a* based on the determined energy balance to regulate the amount of transferred energy. In order to transfer the correct amount of energy, the energy balance and the required amount of energy is determined by means of a determination device including an implanted internal control unit 1015 connected between the switch 1026 and the apparatus 10. The internal control unit 1015 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 1015 is further connected to an internal signal transmitter 1027, arranged to transmit a control signal reflecting the determined required amount of energy, to an external signal receiver 1004*c* connected to the external control unit 1004*b*. The amount of energy transmitted from the external energy source 1004*a* may then be regulated in response to the received control signal.

Alternatively, the determination device may include the external control unit 1004*b*. In this alternative, sensor measurements can be transmitted directly to the external control unit 1004*b* wherein the energy balance and/or the currently required amount of energy can be determined by the external control unit 1004*b*, thus integrating the above-described function of the internal control unit 1015 in the external control unit 1004*b*. In that case, the internal control unit 1015 can be omitted and the sensor measurements are supplied directly to the internal signal transmitter 1027 which sends the measurements over to the external signal receiver 1004*c* and the external control unit 1004*b*. The energy balance and the currently required amount of energy can then be determined by the external control unit 1004*b* based on those sensor measurements.

Hence, the present solution according to the arrangement of FIG. 22 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004*c* may be implemented as separate units using suitable signal transfer means, such as radio, IR (Infrared) or ultrasonic signals. Alternatively, the internal signal transmitter 1027 and the external signal receiver 1004*c* may be integrated in the implanted energy-transforming device 1002 and the external energy source 1004*a*, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 22 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004*c*. Alternatively, the energy balance can be determined by the external control unit 1004*b* instead depending on the implementation, as mentioned above. In that case, the control signal may carry measurement results from various sensors. The amount of energy emitted from the external energy source 1004*a* can then be regulated by the external control unit 1004*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004*a*, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 23:
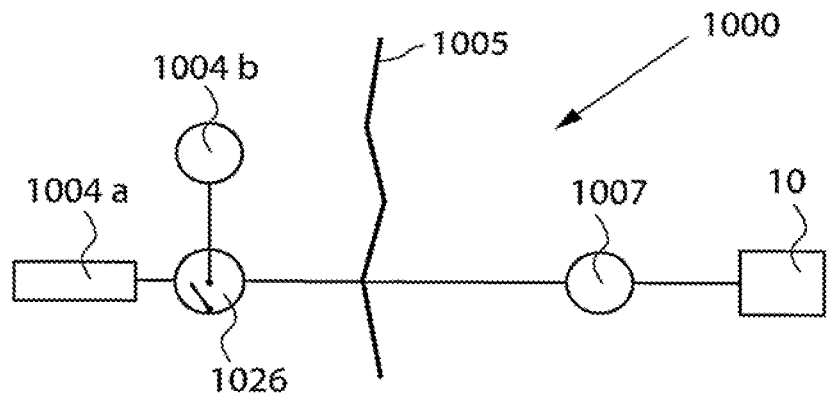

With reference to FIG. 23, although wireless transfer of energy for operating the apparatus has been described above to enable non-invasive operation, it will be appreciated that the apparatus can be operated with wire bound energy as well. Such an example is shown in FIG. 18, wherein an external switch 1026 is interconnected between the external energy source 1004*a* and an operation device, such as an electric motor 1007 operating the apparatus 10. An external control unit 1004*b* controls the operation of the external switch 1026 to effect proper operation of the apparatus 10.

FIG. 24 illustrates different embodiments for bow received energy can be supplied to and used by the apparatus 10. Similar to the example of FIG. 17, an internal energy receiver 1002 receives wireless energy E from an external energy source 1004*a* which is controlled by a transmission control unit 1004*b*. The internal energy receiver 1002 may comprise a constant voltage circuit, indicated as a dashed box "constant V" in the figure, for supplying energy at constant voltage to the apparatus 10. The internal energy receiver 1002 may further comprise a constant current circuit, indicated as a dashed box "constant C" in the figure, for supplying energy at constant current to the apparatus 10.

The apparatus 10 comprises an energy consuming part 10*a*, which may be a motor, pump, restriction device, or any other medical appliance that requires energy for its electrical operation. The apparatus 10 may further comprise an energy storage device 10*b* for storing energy supplied from the internal energy receiver 1002. Thus, the supplied energy may be directly consumed by the energy consuming part 10*a*, or stored by the energy storage device 10*b*, or the supplied energy may be partly consumed and partly stored. The apparatus 10 may further comprise an energy stabilizing unit 10*c* for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the apparatus 10, before being consumed and/or stored by the apparatus 10. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 22 and FIG. 24 illustrate some possible but non-limiting implementation options regarding how the various shown functional components and elements can be arranged and connected to each other. However, the skilled person will readily appreciate that many variations and modifications can be made within the scope of the present invention.

Figure 25:
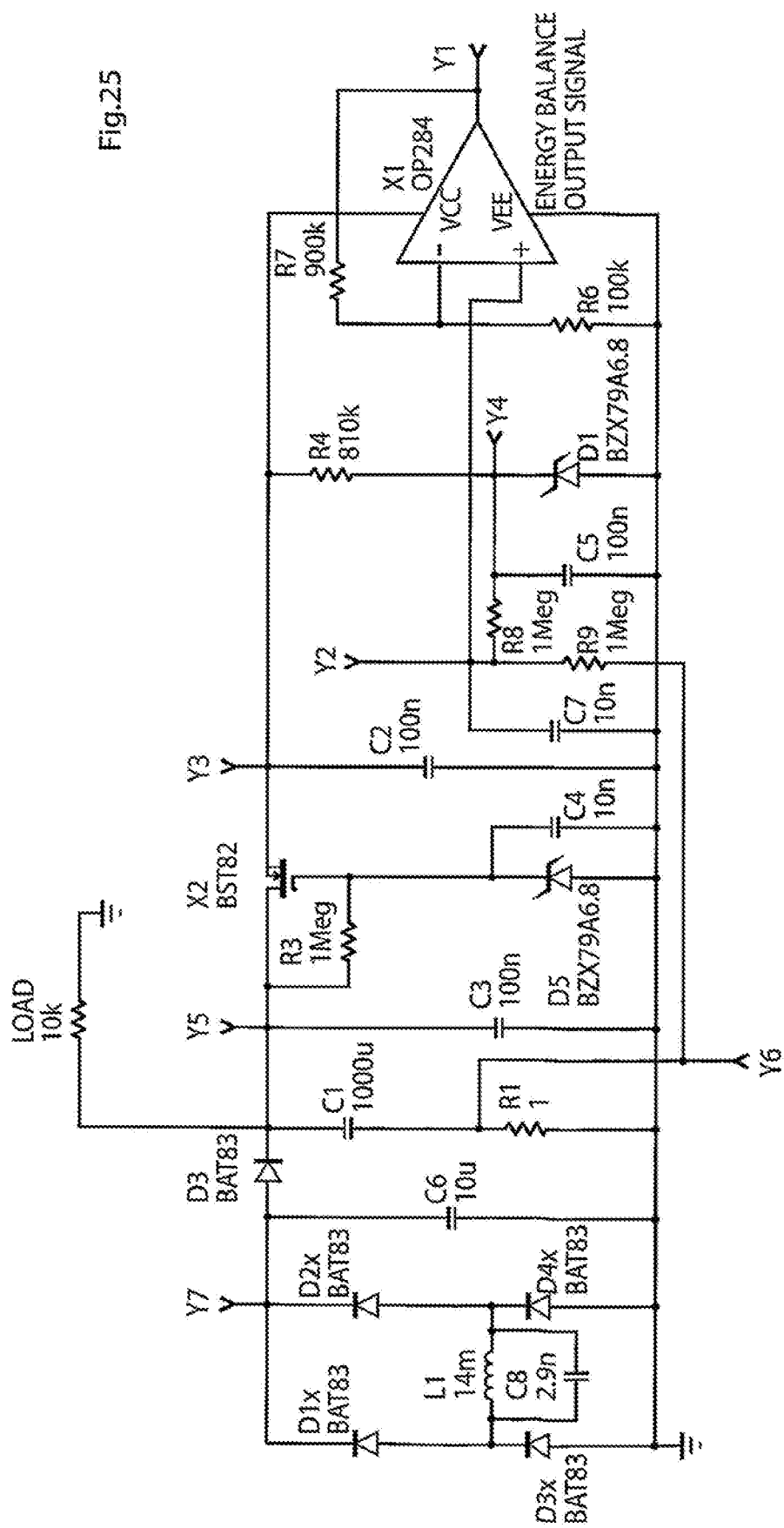
FIG. 25 is a circuit for the arrangement shown in FIG. 19, according to a possible implementation example.

FIG. 25 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount a received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 25 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 3; the transmitting parts of the system are excluded.

The implementation of the general concept of energy balance and the way the information is transmitted to the external energy transmitter can of course be implemented in numerous different ways. The schematic FIG. 25 and the above described method of evaluating and transmitting the information should only be regarded as examples of how to implement the control system.

Circuit Details

In FIG. 25 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 8 could be incorporated in any of the embodiments of FIGS. 11-17 the hydraulic valve shifting device 1014 of FIG. 11 could be incorporated in the embodiment of FIG. 10, and the gear box 1024 could be incorporated in the embodiment of FIG. 9. Please observe that the switch simply could mean any electronic circuit or component.

The embodiments described in connection with FIGS. 22, 24 and 25 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used enemy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the control device controls the transmission of wireless energy based on the detected energy balance change The determination device is adapted to detect a difference between energy received by the internal energy receiver and energy used for the implantable energy consuming components of the apparatus, and the control device controls the transmission of wireless energy based on the detected energy difference.

The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 26-29 show in more detail block diagrams of four different ways of hydraulically or pneumatically powering an implanted apparatus according to the invention.

Figure 26:
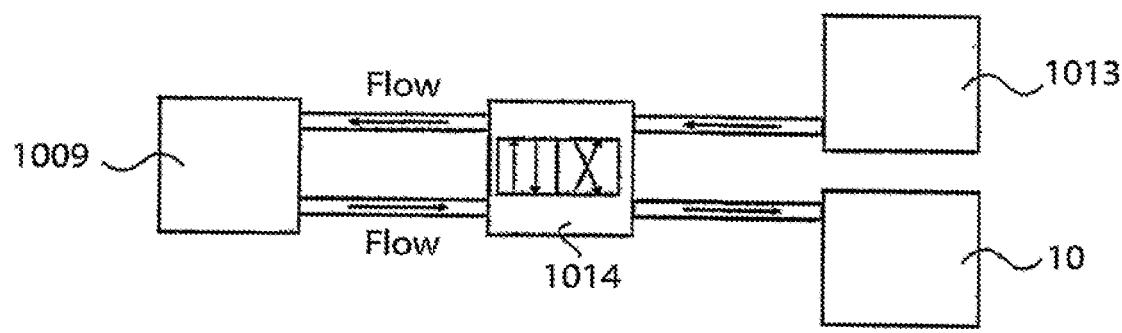
FIGS. 26-32C show various ways of arranging hydraulic or pneumatic powering of an apparatus implanted in a patient.

FIG. 26 shows a system as described above with. The system comprises an implanted apparatus 10 and farther a separate regulation reservoir 1013, a one way pump 1009 and an alternate valve 1014.

Figure 27:
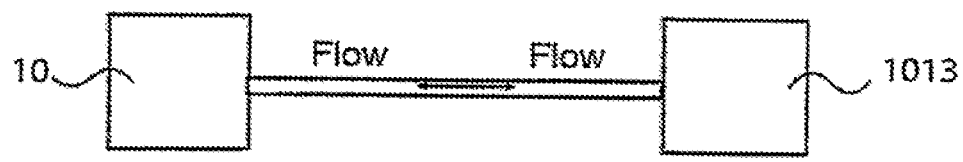

FIG. 27 shows the apparatus 10 and a fluid reservoir 1013. By moving the wall of the regulation reservoir or changing the size of the same in any other different way, the adjustment of the apparatus may be performed without any valve, just free passage of fluid any time by moving the reservoir wall.

Figure 28:
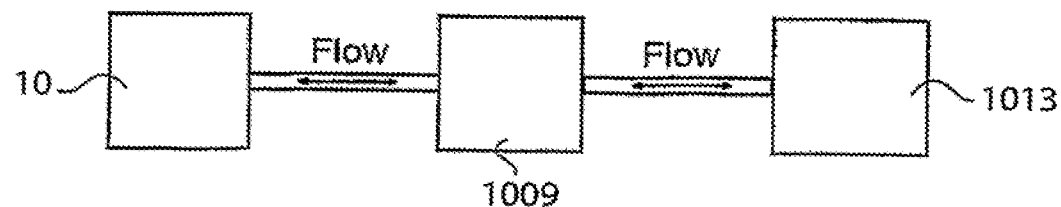

FIG. 28 shows the apparatus 10, a two way pump 1009 and the regulation reservoir 1013.

Figure 29:
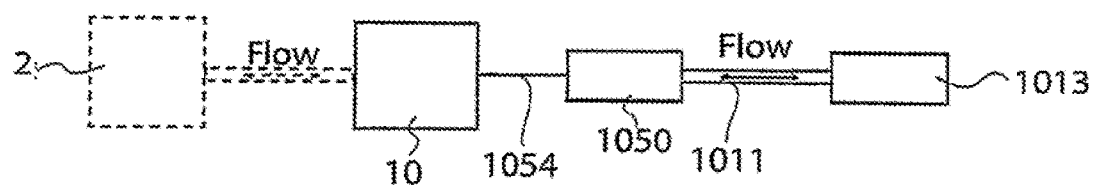

FIG. 29 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded wider the control of the servo reservoir 1050.

The servo reservoir 1050 can also be part of the apparatus itself.

Figure 30A:
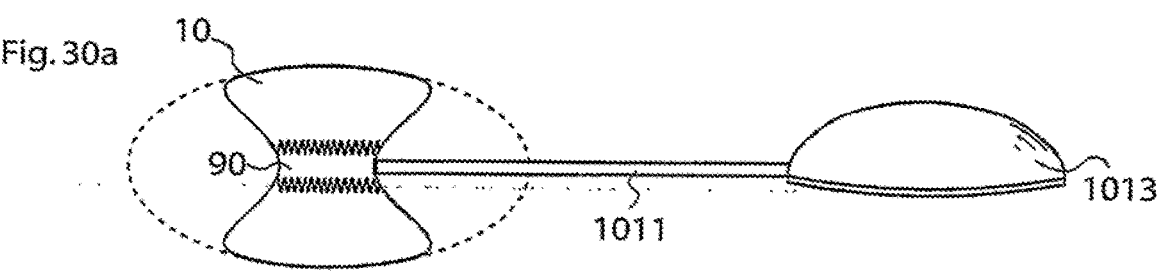
Figure 30B:
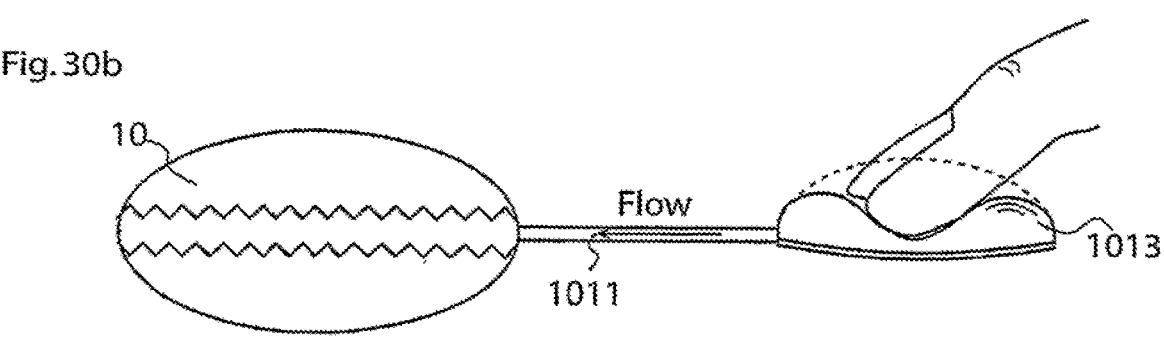
Figure 30C:
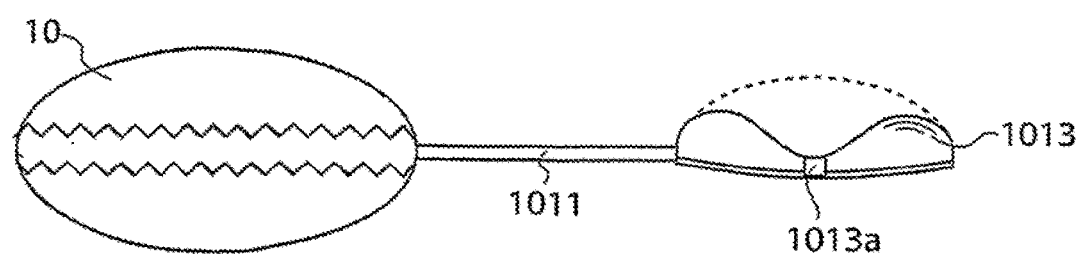
Figure 31:
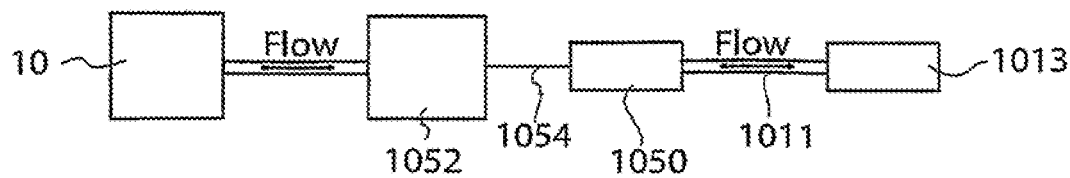

In one embodiment, the regulation reservoir is placed subcutaneous under the patient's skin and is operated by pushing the outer surface thereof by means of a finger. This system is illustrated in FIGS. 30a-c. In FIG. 30a, a flexible subcutaneous regulation reservoir 1013 is shown connected to a bulge shaped servo reservoir 1050 by means of a conduit 1011. This bellow shaped servo reservoir 1050 is comprised in a flexible apparatus 10. In the state shown in FIG. 30a, the servo reservoir 1050 contains a minimum of fluid and most fluid is found in the regulation reservoir 1013. Due to the mechanical interconnection between the servo reservoir 1050 and the apparatus 10, the outer shape of the apparatus 10 is contracted, i.e., it occupies less than its maximum volume. This maximum volume is shown with dashed lines in the figure.

FIG. 30b shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the apparatus 10 so that it occupies its maximum volume, thereby stretching the stomach wall (not shown), which it contacts.

The regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 31 and 32a-c. The block diagram shown in FIG. 31 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contactable cavity is in turn controlled by the larger adjustable reservoir 1052 by supply of hydraulic fluid from the larger adjustable reservoir 1052 in fluid connection with the apparatus 10.

Figure 32A:
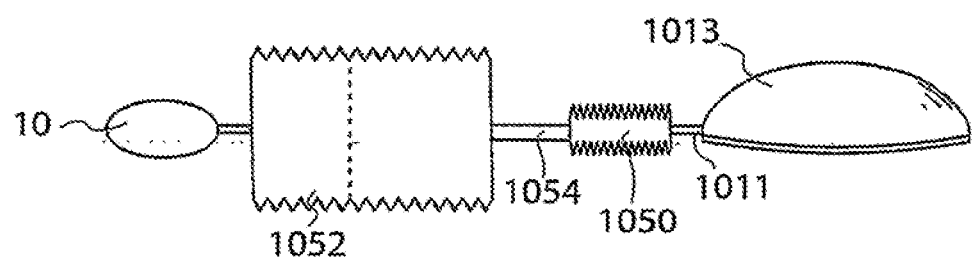
Figure 32B:
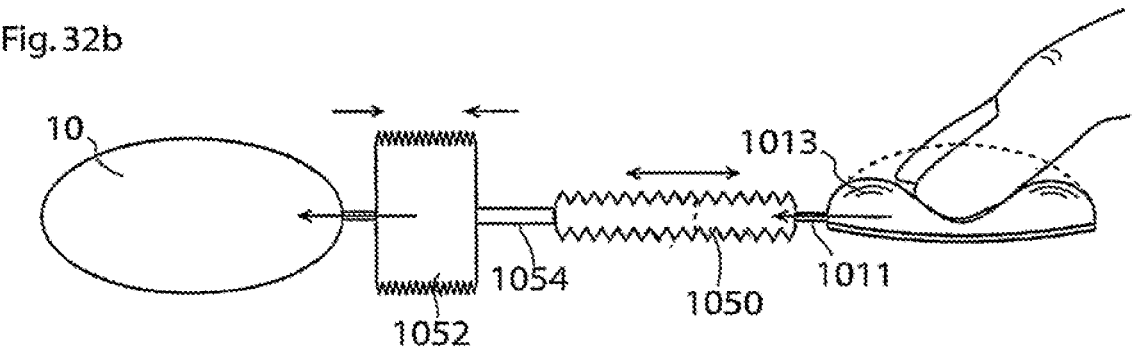
Figure 32C:
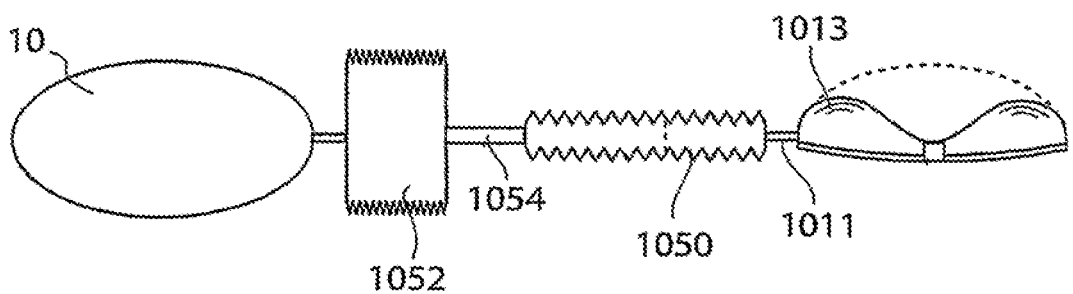

An example of this embodiment will now be described with reference to FIG. 32a-c. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 31a, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher three and this creates a movement of a larger total area with less force per area unit.

Like in the previous embodiment described above with reference to FIGS. 30a-c, the regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

The invention claimed is:

1. A system for treating urinary retention of a mammal patient by discharging urine from a urinary bladder, comprising:
   an implantable powered member adapted to exert a force from outside on a selected part of the urinary bladder in order to discharge urine from the urinary bladder;
   at least one implantable restriction device for temporary restriction of a ureter; and
   a control device for controlling an operation of the powered member and for controlling the at least one restriction device to close the ureter when discharging urine from the urinary bladder.

2. A system according to claim 1, further comprising a second restriction device for temporary restriction of a second ureter.

3. A system according to claim 1, comprising an artificial urinary sphincter, wherein the at least one restriction device, controlled by the control device performs as a urinary sphincter.

4. A system according to claim 1, wherein the control device, comprises a source of energy for operating energy consuming parts of the apparatus, wherein said powered member is one of the energy consuming parts.

5. A system according to claim 4, wherein the control device is adapted to be implanted at least partially subcutaneously or in an abdomen or in a pelvic region.

6. A system according to claim 5, wherein the control device is adapted to be implanted both subcutaneously and in an abdominal cavity, said control device comprising at least two parts adapted to be connected, when implanted.

7. A system according to claim 1, wherein the powered member comprises a contacting part adapted to contact a surface part of the urinary bladder.

8. A system according to claim 7, wherein the powered member comprises at least one operable pressurizer connected to the contacting part in an arrangement, wherein operating the at least one operable pressurizer provides compression or release of the urinary bladder.

9. A system according to claim 1, wherein said force is exerted at least partly against a support structure.

10. A system according to claim 9, wherein said support structure is adapted to support against at least one of a bone or other human tissue.

11. An apparatus adapted to treatment of urinary retention of a mammal patient by discharging urine from a urinary bladder, comprising:
   an implantable powered member with a urinary bladder surface contact part, said powered member being adapted to exert a force from outside on a selected part of the urinary bladder in order to discharge urine from the urinary bladder;
   a support structure adapted to support against at least one of, a bone or other human tissue, and a control device for controlling an operation of the powered member,
   wherein the force of the powered member exerted on the urinary bladder is at least partly exerted against the support structure when discharging urine from the urinary bladder.

12. An apparatus according to claim 11, wherein the powered member comprises at least one operable pressurizer connected to a contacting part in an arrangement, wherein operating the at least one operable pressurizer provides compression or release of the urinary bladder.

13. An apparatus according to claim 12, wherein the at least one operable pressurizer comprises an operation device attached to a support device adapted to be fixated to the urinary bladder wall.

14. An apparatus according to claim 13, wherein the support device is generally ring-shaped or having an intermittent ring-shape, said support device extending along a periphery of the urinary bladder.

15. An apparatus according to claim 11, wherein the powered member is mechanically operated to provide compression or release of the urinary bladder.

16. An apparatus according to claim 15, comprising at least one movable arm extending from an operation device to the urinary bladder surface contact of the powered member, said surface contact part being adapted to contact a surface part of the urinary bladder, wherein the operation device is adapted to displace the at least one movable arm towards the urinary bladder in order to discharge urine from the urinary bladder, wherein the operation device comprises a motor adapted to displace the at least one movable arm.

17. An apparatus according to claim 16, wherein the operation device is adapted to be fixated to human tissue, wherein the operation device is adapted for fixation to at least one of: a pubic bone, a urinary bladder or an abdominal wall or a pelvic wall.

18. An apparatus according to claim 11, wherein the apparatus further comprises at least one implantable restriction device for temporary restriction of a ureter.

19. An apparatus according to claim 18, further comprising a second restriction device for temporary restriction of a second ureter.

20. An apparatus according to claim 11, comprising an artificial urinary sphincter, wherein at least one restriction device, controlled by the control device performs as a urinary sphincter.

* * * * *